_United States Patent_ [19]

Burke et al.

[11] Patent Number: 5,404,659
[45] Date of Patent: Apr. 11, 1995

[54] SHOE INSOLE/MIDSOLE FOR FOOT REHABILITATION HAVING A DOME SHAPED STRUCTURE

[75] Inventors: Robert G. Burke, Scarborough; Roy J. W. Gardiner, Toronto, both of Canada; Scott R. Kantro, New York, N.Y.

[73] Assignee: Tarsatch, Inc., Scarborough, Canada

[21] Appl. No.: 261,877

[22] Filed: Jun. 17, 1994

Related U.S. Application Data

[63] Continuation of Ser. No. 70,236, Jun. 2, 1993, abandoned.

[30] Foreign Application Priority Data

Jun. 2, 1992 [CA] Canada ................ 2070274

[51] Int. Cl.$^6$ ................ A61F 5/14
[52] U.S. Cl. ................ 36/176; 36/43; 36/173
[58] Field of Search ............ 36/173, 174, 176, 145, 36/166, 180, 43, 44, 91, 28, 30 R

[56] References Cited

U.S. PATENT DOCUMENTS

| | | | |
|---|---|---|---|
| 1,605,985 | 11/1926 | Rasmussen . | |
| 1,676,162 | 7/1928 | Schiller . | |
| 1,709,852 | 4/1929 | Hurley | 36/145 |
| 1,710,936 | 4/1929 | May | 36/145 |
| 1,867,431 | 7/1932 | Wood | 36/145 |
| 1,953,048 | 3/1934 | Crompton | 36/145 |
| 2,046,190 | 6/1936 | Silver . | |
| 2,084,455 | 6/1937 | Reed . | |
| 2,161,565 | 6/1939 | Freda | 36/180 |
| 2,383,583 | 8/1945 | Becker | 36/180 |
| 2,423,622 | 7/1947 | Samblanet | 36/161 |
| 3,265,071 | 8/1966 | Kirchner et al. | 36/145 |
| 3,905,376 | 9/1975 | Johnson et al. . | |
| 4,346,525 | 8/1982 | Larsen et al. | 36/145 |
| 4,360,027 | 11/1982 | Friedlander et al. . | |
| 4,442,612 | 4/1984 | Hauser . | |
| 4,541,184 | 9/1985 | Leighton | 36/180 |
| 4,677,766 | 7/1987 | Gudas | 36/43 |
| 4,697,361 | 10/1987 | Ganter et al. . | |
| 4,716,662 | 1/1988 | Bar . | |
| 4,718,179 | 1/1988 | Brown . | |
| 4,729,179 | 3/1988 | Quist, Jr. . | |
| 4,747,410 | 5/1988 | Cohen . | |
| 4,759,357 | 7/1988 | Allart et al. . | |
| 4,841,648 | 6/1989 | Shaffer et al. . | |
| 5,138,774 | 8/1992 | Sarkozi | 36/160 |

FOREIGN PATENT DOCUMENTS

| | | | |
|---|---|---|---|
| 849155 | 11/1939 | France | 36/176 |
| 83595 | 12/1919 | Switzerland | 36/176 |

Primary Examiner—Paul T. Sewell
Assistant Examiner—Thomas P. Hilliard
Attorney, Agent, or Firm—Sherman & Shalloway

[57] ABSTRACT

A shoe insole-midsole device configured to fit the profile of the human foot with a distinctive toe end and a distinctive heel. The midfoot section of the insole/midsole device is characterized by an asymmetrical domed structure that is presented to the plantar aspect of the foot at a location found to be the anatomical apex of the foot's arch system. The domed structure displays physical properties such as to catalyze muscle group balancing by utilizing the body's proprioceptive feedback mechanisms. The net result will be a more structurally sound foot capable of more energy efficient and less injury inducing use. In addition to the predominant dome characteristic, the insole/midsole is also typified by a posterior most skiving which reduces impact velocity, thus easing the introduction of the dome characteristic to the plantar aspect of the foot.

16 Claims, 4 Drawing Sheets

SHOE INSOLE/MIDSOLE FOR FOOT REHABILITATION HAVING A DOME SHAPED STRUCTURE

This application is a continuation of application Ser. No. 08/070,236, filed Jun. 2, 1994, now abandoned.

BACKGROUND OF THE INVENTION

The present invention relates to a shoe insole or midsole unit that utilizes proprioceptive feedback mechanisms in the human body to increase the structural integrity of the human foot.

It is a common belief within the realm of professionals dealing with gait related pathologies that a large majority of persons will, at some time in their lives, suffer some form of gait related pain or dysfunction. It is also well accepted that in the majority of cases the mechanism underlying the pathology, injury, or dysfunction can be biomechanically related to the interface of the foot and ground, during the support phase of the gait cycle.

In simplest terms, peoples' feet, for speculative reasons, are in many cases not functioning in an ideal manner when those persons are walking or running.

Many papers have been presented over the last 40 and more years, in the field of podiatry and biomechanics, that describe, what is believed to be, how the foot should interface with the ground, and what magnitude of motions are characterized as normal. In reaction to these findings the concept of introducing appliances, or orthotics, into footwear to brace against excess motion was introduced.

The essence of these appliances was that a physical obstacle could be placed in the footwear to act as a brace against unwanted motion, as diagnosed by a professional in an associated field. Unfortunately efforts made to brace against unwanted motion are accompanied by disuse of the associated muscles that had at one time either caused the motion, or tried to regulate that motion. These muscles, and/or muscle groups will atrophy, or weaken, simply because they are not being used. This form of disuse atrophy is well documented in relation to both bone and muscle.

The relationship between the amount of unwanted motion and muscle strength are inversely related. That is, the weaker the muscles become, the more of the unwanted movement will occur. The inserted appliances therefore promote a weakening of associated muscles, by acting as a brace, and become an object which the body will become dependent upon. The lifestyle of the affected persons will now be such that non discomfort related walking or running is virtually impossible without the insertion of the appliance into the chosen footwear.

In other fields of medicine it is well accepted that injuries to bones, connective tissue and muscles can be rehabilitated, and that a balance in muscle strength and flexibility is important. It is also well recognized that movement of body segments is essential in increasing both strength and flexibility, and that bracing does not promote this. It is also well accepted in all medical fields that the foot and lower limb are composed of bones, connective tissue, and muscles. In these fields it also is accepted that the human body possesses neuromuscular feedback mechanisms which are such that the body's tendencies are to maintain a homeostatic existence. One of these proprioceptive feedback mechanisms functions on the basis of applied pressure. Applied pressure perpendicular to a muscle body's line of action creates tension in the golgi tendon organ thus stimulating the proprioceptive feedback mechanism. The human body will display tendencies to move away from exerted pressures which are uncomfortable. By utilizing this proprioceptive mechanism it is possible to create an environment in which muscles will strengthen themselves as a means of reducing the applied pressure. This mechanism is utilized in the design of this invention such that the associated musculature of the foot will strengthen itself, thus improving its structural integrity and reducing its dependency on artificial modes of bracing.

It is the object of the present invention to provide a novel approach to providing the foot with a means of attaining normal biomechanical values, while at the same time strengthening the associated foot's structural integrity such that any dependency upon footwear bracing, for pain free gait, is eliminated.

Numerous other devices exist or have been invented but these devices are dependent upon the conventional ideology of bracing the foot, an action felt to encourage musculoskeletal atrophy, as well as create dependencies upon bracing devices, or are simply designed to provide short term comfort. Examples of these are U.S. Pat. Nos. 2,084,455 (Reed), 2,046,190 (Silver), 4,716,662 (Bar), 1,605,985 (Rasmussen), 4,442,612 (Hauser), 3,905,376 (Johnson), 1,676,162 (Schiller), 4,759,357 (Allart), 4,747,410 (Cohen), 4,841,648 (Shaffer), 4,697,361 (Ganter), 4,718,179 (Brown), 4,729,179 (Quist) and 4,360,027 (Frielander). Of equal importance when looking at these devices is the lack of presentation of a concept where principles of proprioceptive feedback are used. Similarly, it is also important to note in the case of said invention, the foot is looked upon, mechanically, as being composed of 5 individual arches, corresponding to the 5 metatarsals, each having an anterior end at a metatarsal head, and a posterior end between the lateral and medial tubercles of the calcaneus. These 5 arches intersect at a common point creating a dome structure within the foot itself. The common point of intersection is the articulation of the cuboid, navicular, and lateral cuneiform bones of the foot. This intersection point will hereinafter be referred to as the "apex of the foot's arch system." The unsupported height of the apex of the foot's arch system allows the foot to function as a dynamic dome structure, never sacrificing structural integrity as it adapts to changes in the ground surface.

Although the concept of bracing has produced some favorable results, these results are dependent upon the use of the appliance, once the appliance has been removed the predisposition to injury is greatly magnified.

DETAILED DESCRIPTION OF THE PREFERRED EMBODIMENT

Figure 1:
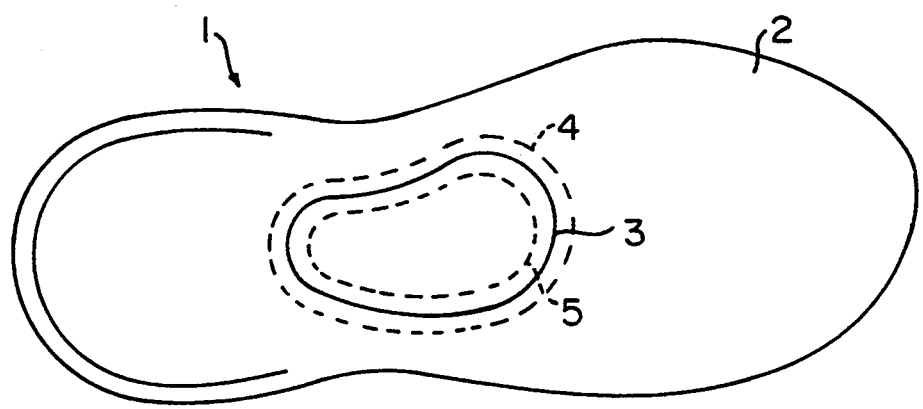
FIG. 1, a top view of the insole or midsole unit.

In one aspect of the invention there is provided a foot rehabilitative system comprising an insole or midsole 1 defining a surface to contact the foot, a central region (arch rehabilitative catalyst) 3 of said surface being complementary alignable with the apex of the foot's arch system 9 (see FIG. 7) said central region 3 having oppositely disposed surface positions extending laterally outwardly and downwardly from a maximum (apex 9) (see FIGS. 7,8) in relation to said surface.

The arch rehabilitative catalyst 3 of said insole or midsole 1 described shall encompass an area defined by an anterior most arc 17, a posterior most arc 18, a medial arc 19, and a lateral arc 20, said anterior arc 17 is such that its apex corresponds with the area lateral to the 2nd metatarsal and medial to the 3rd metatarsal and not extend in an anterior direction more than 70% of the foot length, and not less than 60%, said posterior most arc 18 is such that its apex corresponds with an area medial to the lateral tubercle of the calcaneus and lateral to the medial tubercle, and not extend in a posterior direction at any point less than 15% of the foot's total length or any point greater than 25% of the foot's total length, said lateral and medial arcs are such that at no point do they exceed the medial and lateral boundaries created by the foot itself, said arch rehabilitative catalyst will have its entirety within the periphery set by the metatarsal heads, calcaneus, and lateral and medial borders of the foot. There is therefore a set minimum periphery 5 and a maximum periphery 4 delineating location of said arch rehabilitative catalyst 3.

Figure 7:
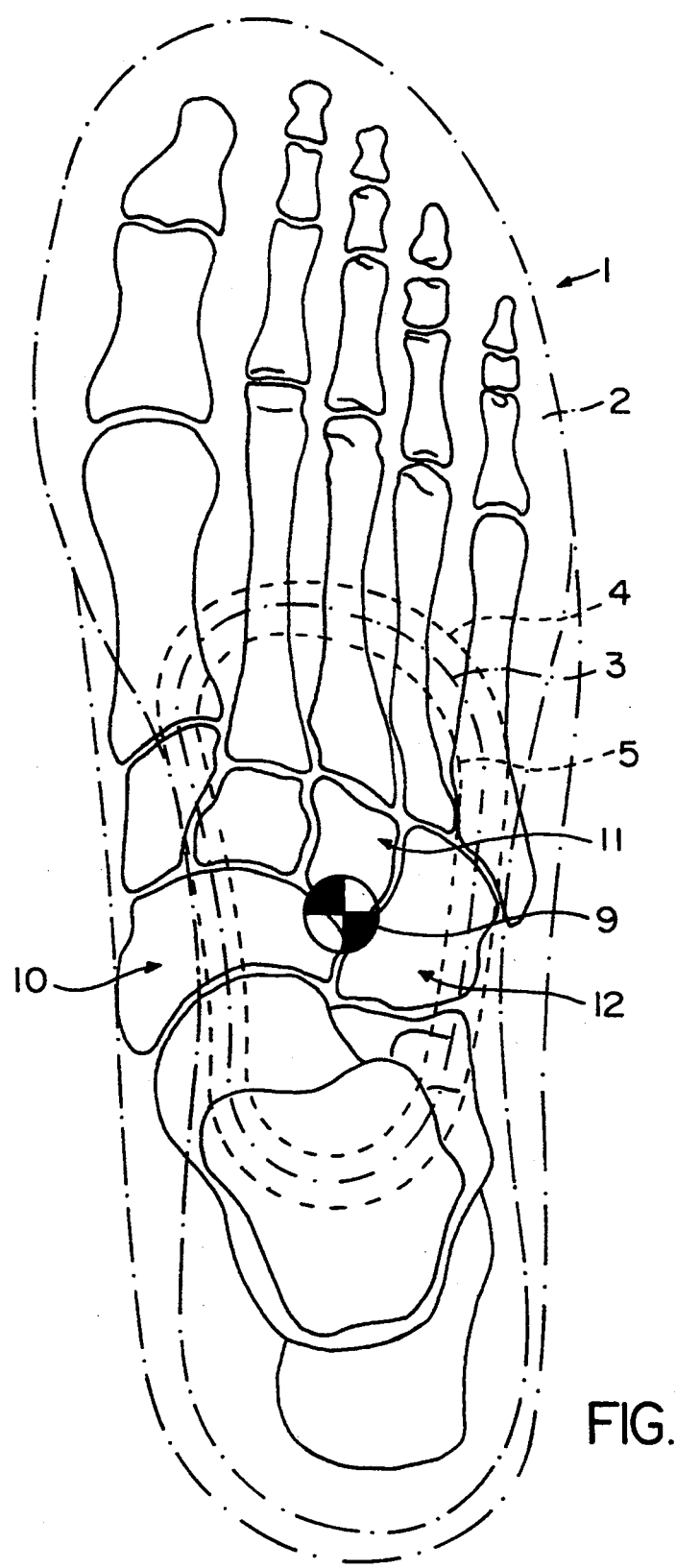
FIG. 7, a top view illustrating the placement of a human foot skeleton relative to the insole or midsole unit of FIG. 1.
Figure 8:
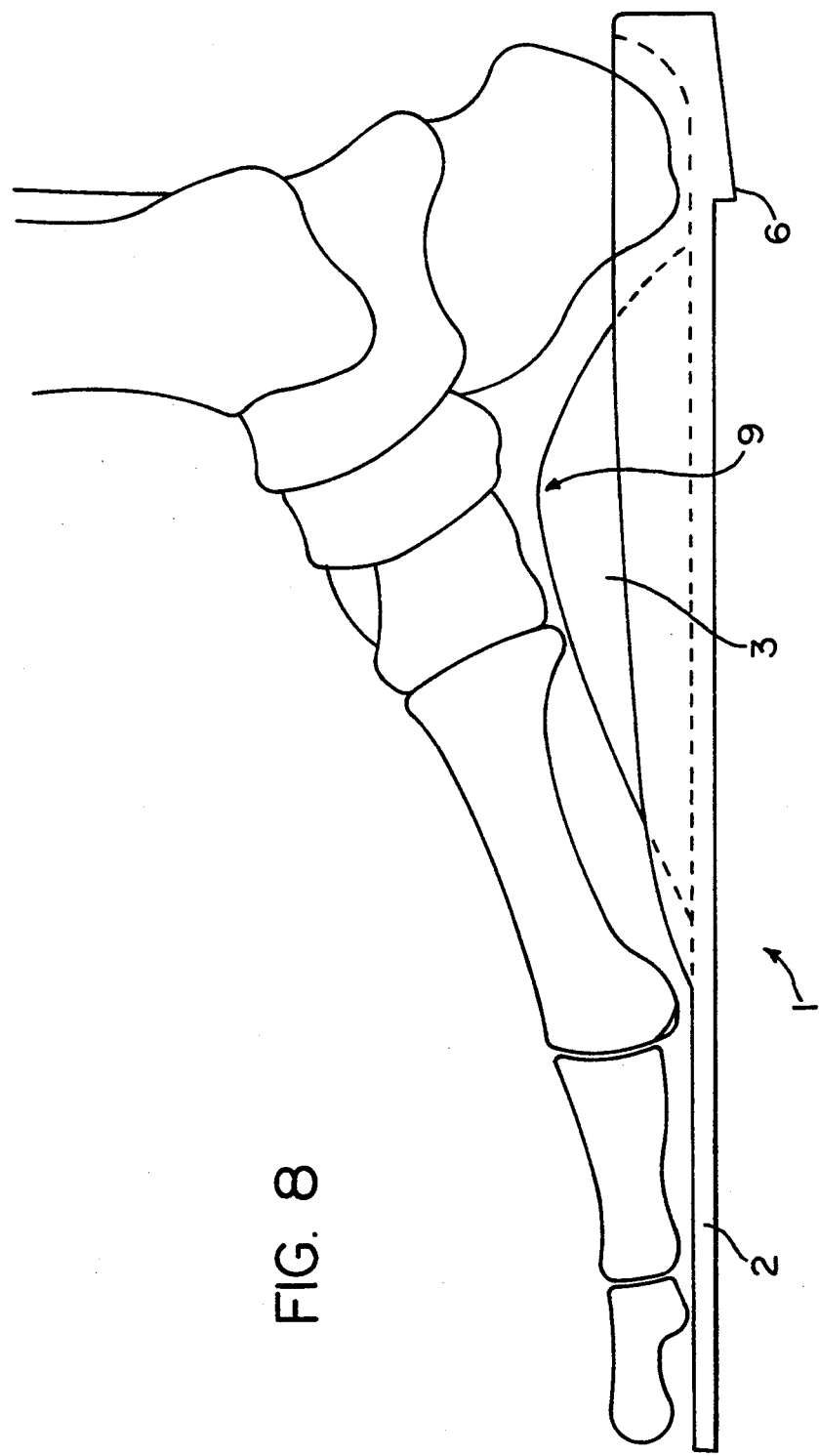
FIG. 8, a sagittal view of FIG. 1 with the placement of the human foot skeleton sitting on the top of the unit.

This aspect of the invention 1 is presented in FIG. 1 and FIG. 7 which clearly outlines the boundaries of said arch rehabilitative catalyst; wherein the insole or midsole 1 is made up of the body 2 and the arch rehabilitative catalyst 3, displaying a maximum boundary 4, and a minimum boundary 5.

Figure 2:
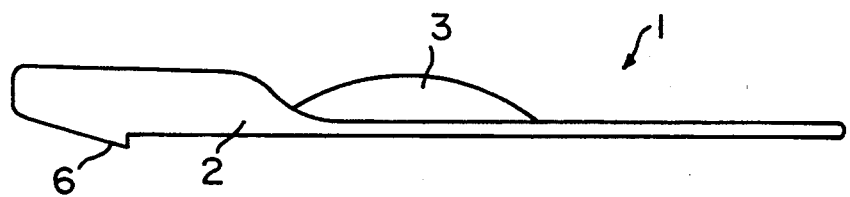
FIG. 2, a sagittal view of FIG. 1.

From a sagittal and frontal plane view the geometric configuration of said arch rehabilitative catalyst 3 will be dome like, with its apex 9 corresponding with the articulation of the lateral cuneiform 11, cuboid 12 and navicular 10 bones of the foot. This aspect of the invention is presented in FIG. 2 and FIGS. 7 and 8 wherein the body 2, the arch rehabilitative catalyst 3, and a tapered heel step 6 to be discussed later, are shown.

This will guarantee that the foot itself will be subjected to an arch rehabilitative catalyst 3 that will allow uninhibited tri-planar movement of the foot about an apex functioning as a pivot point. The shape and position of the dome like arch rehabilitative catalyst 3 is such that an upwardly directed pressure (and mild discomfort) is created on the plantar aspect of the apex of the foot's foot, at the arch region, in response to this pressure the musculature of the foot will strengthen in effort to lift the foot and thus reduce the pressure, thereby enhancing the structural integrity of the foot's arch system.

In another aspect of the invention said arch rehabilitative catalyst 3 described should display density, compression and rebound characteristics such that when the catalyst 3 is subjected to the vertical forces common to ambulatory running, which represent approximately 2.5 times body weight, said catalyst 3 will deflect between 40% and 60% of its maximum height, vertical forces equal to 1 body weight should create no compression of said arch rehabilitative catalyst 3, ideal apex 9 height of said arch rehabilitative catalyst is between 5.28% and 7.6% of the total foot length with the ideal being 6.33%. With vertical force intermediate between 1 and 2.5 times body weight the deflection will be correspondingly between 0% and 40% to 60%.

Figure 3:
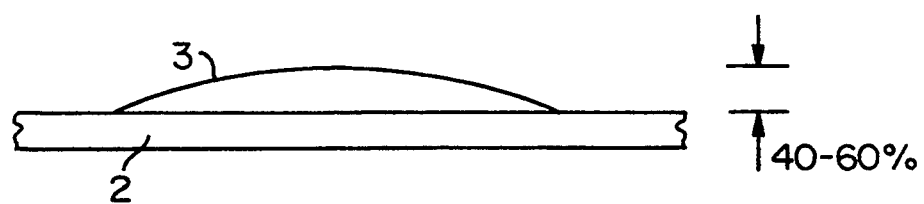
FIG. 3, a part section of FIG. 2 subjected to 2.5 times body weight.
Figure 4:
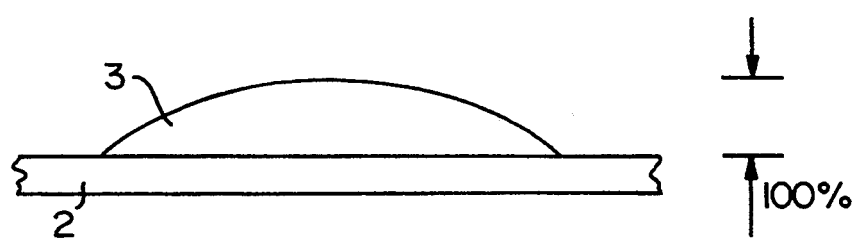
FIG. 4, a part section of FIG. 2 subjected to 1 body weight.

The aspect of the invention is presented in FIG. 3 and FIG. 4 wherein the body 2 and the arch rehabilitative catalyst 3 are shown in a 2.5 times body weight example, and a 1 body weight example, respectively.

The compression, density, and rebound characteristics described above ensure three primary functions:

I) The rebound characteristics ensure that the arch rehabilitative catalyst will return to its original height, thereby ensuring contact with the apex of the foot's arch system. This contact provides a catalyst to stimulate the proprioceptive mechanism necessary for the proper restructuring of the foot's arch systems' musculoskeletal characteristics.

II) The compressive characteristics allow the human foot's arch system to deflect in a natural manner and thereby the human arch system can act as a natural cushioning mechanism, while preventing any bracing effects from occurring.

III) The compressive characteristics allow the human foot arch system to deflect in a natural manner thereby allowing eccentric contractions of the foots' plantar musculature to occur. This regulates the velocity of arch deflection as well as allows the series and parallel spring characteristics of the muscle to store energy and contribute that stored energy to effective propulsion.

When introduced as a rehabilitative system said arch rehabilitative catalyst 3 may be required to be replaced gradually with materials displaying different compression, rebound, and density characteristics, as dictated by progressive musculoskeletal changes. For example a flat footed person (a person whose skeleton does not possess an arch system with any functional integrity) would begin with a low density catalyst that would not generate too much force on the plantar aspect of the arch system as to create injury. As the foot responds to the arch rehabilitative catalyst, to maintain stimulation of the proprioceptive feedback mechanism a catalyst of higher density will be substituted to ensure ongoing proprioceptive stimulation, up until the point in time when the person's arch system displays characteristics that can be attributed to that of ideal foot structure. In this manner a flat foot (low arched, pes planus) will strengthen and remodel such that a functional arch system will be present, as well as promote a balancing between the opposing musculature of the foot.

In contrast to this, a rigid, high arched foot (pes cavus) would require a catalyst of a higher density with a lower degree of compression characteristics. This would ensure constant proprioceptive stimulation to the point of inducing muscle laxity through continuous muscle firing. This would in time promote increases in the flexibility of the foot as well as a balancing between the opposing musculature of the foot.

The absolute, non weight bearing height of arch rehabilitative catalyst 3 should be the same regardless of body weight and arch height. The characteristics that do change are the density, compression, and rebound properties in accordance to foot morphology.

Because density is a function of mass and volume it is difficult to quantify in this dynamic situation. The volume will change due to compressive characteristics of the arch rehabilitative catalyst during motion, and the applied mass is dependent upon body type, which is not standard. These intra and inter subject inconsistencies make it virtually impossible to correlate arch rehabilitative catalyst density to body weight. A third variable comes into play, this is the musculoskeletal characteristics of the foot, and this is probably the most important variable to account for, and it itself is made up of at least three variables. These are osseous geometry, muscle strength, and ligament laxity. These are also virtually impossible to measure and categorize, as each contributes differently in every foot.

The following tables reveal the ideal arch height, and an appropriate arch height range for conventional men's and ladies' U.S. shoe sizes, based on accepted last bottom measurements and foot lengths.

| MEN'S | | | | |
|---|---|---|---|---|
| Shoe Size (U.S.) | Foot Length (mm) | Ideal Arch (mm) | Minimum Height | Maximum Height |
| 6.5 | 255.08 | 16.16 | 13.47 | 19.39 |
| 7.0 | 259.31 | 16.43 | 13.69 | 19.72 |
| 7.5 | 263.54 | 16.70 | 13.92 | 20.04 |
| 8.0 | 267.77 | 16.96 | 14.13 | 20.35 |
| 8.5 | 272.00 | 17.23 | 14.36 | 20.68 |
| 9.0 | 276.23 | 17.50 | 14.58 | 21.00 |
| 9.5 | 280.46 | 17.79 | 14.82 | 21.34 |
| 10.0 | 284.69 | 18.04 | 15.03 | 21.64 |
| 10.5 | 288.92 | 18.30 | 15.25 | 21.96 |
| 11.0 | 293.15 | 18.57 | 15.47 | 22.28 |
| 11.5 | 297.38 | 18.84 | 15.70 | 22.61 |
| 12.0 | 301.61 | 19.11 | 15.92 | 22.93 |
| 13.0 | 310.07 | 19.64 | 16.37 | 23.56 |

| LADIES | | | | |
|---|---|---|---|---|
| Shoe Size (U.S.) | Foot Length (mm) | Ideal Arch (mm) | Minimum Height | Maximum Height |
| 5.0 | 233.00 | 14.76 | 12.30 | 17.71 |
| 5.5 | 237.23 | 15.03 | 12.52 | 18.04 |
| 6.0 | 241.46 | 15.30 | 12.75 | 18.36 |
| 6.5 | 245.69 | 15.56 | 12.97 | 18.68 |
| 7.0 | 249.92 | 15.83 | 13.19 | 18.99 |
| 7.5 | 254.15 | 16.10 | 13.42 | 19.32 |
| 8.0 | 258.38 | 16.39 | 13.64 | 19.64 |
| 8.5 | 262.61 | 16.64 | 13.87 | 19.96 |
| 9.0 | 266.84 | 16.90 | 14.08 | 20.28 |
| 9.5 | 271.07 | 17.17 | 14.31 | 20.60 |
| 10.0 | 275.30 | 17.44 | 14.53 | 20.93 |
| 10.5 | 279.53 | 17.71 | 14.76 | 21.25 |
| 11.0 | 283.76 | 17.98 | 14.82 | 21.58 |

In another aspect of the invention, the foot rehabilitative system 1 as described has a posterior aspect of said insole or midsole comprised of a tapered step 6, wherein the maximum step thickness corresponds with the sagittal plane midline of the calcaneus and tapers to a level equal to the minimum thickness of said insole or midsole 1 at the posterior most part of said insole or midsole 1. This aspect of the invention is presented in FIG. 2 and FIG. 8, wherein the tapered step 6 is shown, as well as the body 2, and arch rehabilitative catalyst 3.

In this the tapered step 6 serves to reduce the velocity of the foot once it is planted on the ground at heel strike. This functions as a precaution by allowing the foot to be slowly lowered unto the arch rehabilitative catalyst. In doing so, any risk of impact related injury to the foot's arch system is reduced, as well as increasing the initial comfort of the insole or midsole 1 by allowing the pressure application to be more gradual.

Figure 5:
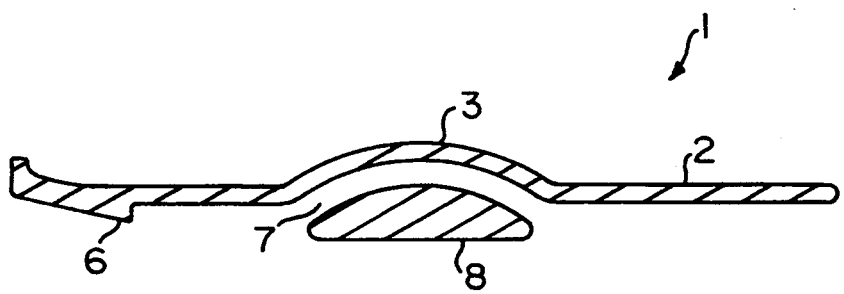
FIG. 5, a cross sectional depicting a proposed finished insole or midsole unit comprising two components.

In another aspect of the invention, namely that concerning manufacturing, there are a number of options available. The preference would be the creation of an insole or midsole body 2 of a polyethylene, polyurethane, foam rubber or ethyl vinyl acetate compound, or a material displaying the necessary properties, by injection molding, vacuum forming, press molding, or a like operation. To accompany this would be an arch rehabilitative catalyst 3 insert 8 of similar material and individual properties as those previously presented, and manufactured by a similar operation as that of the body 2. The appropriate insert 8 would then be applied to the insole or midsole 2, by one of the many forms of appropriate adhesives, by that person or by a professional from a related field. This aspect of the invention is presented in FIG. 5 wherein the insole or midsole 1, body 2, tapered step 6, arch rehabilitative catalyst receptacle 7, and arch rehabilitative catalyst 8, are shown as a cross section.

Figure 6:
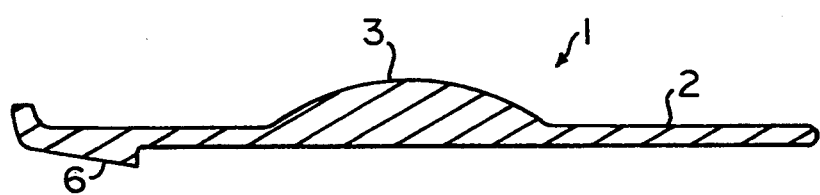
FIG. 6, a cross sectional depicting the finished insole or midsole unit fabricated as a one piece unit.

An option to this method of production would be fabrication of a one piece unit insole or midsole body 2 in which the arch rehabilitative catalyst 3 is able to display characteristics previously typified. These aspects of the invention are presented in FIG. 6 wherein the insole or midsole 1, body 2, arch rehabilitative catalyst 3, and tapered step 6 are shown as a 1 piece unit in cross section.

While the present invention has been described with some degree of particularity, it should be appreciated that those skilled in the art will recognize various modifications and embodiments thereof within the spirit and scope of the invention and, therefore, the present invention is defined by the following claims construed in light of the foregoing and the prior art, and any equivalents thereof.

We claim:

1. A foot/arch rehabilitative insole or midsole unit which comprises a dome shaped structure interfacing with the plantar aspect of a human foot with the apex of the dome shaped structure fitting with the articulation of the lateral cuneiform, cuboid and navicular bones of the foot to allow uninhibited tri-planar movement of the foot about the apex functioning as a pivot point, said dome shaped structure exerting an upwardly directed pressure in the plantar aspect of the foot, at the arch region thereof, thereby creating tension in the golgi tendon organ.

2. A foot/arch rehabilitative insole or midsole unit as defined in claim 1 wherein the dome shaped structure has a distinct area defined by an anterior most arc, a posterior most arc, a medial arc, and a lateral arc, said anterior arc being dimensioned such that its apex corresponds with the area lateral to the 2nd metatarsal and medial to the 3rd metatarsal and does not extend in an anterior direction more than 70% of the foot length, nor less than 60%, said posterior most arc being dimensioned such that its apex corresponds with an area medial to the lateral tubercle of the calcaneus and lateral the medial tubercle, and does not extend in a posterior direction at any point less than 15% of the foot's total length or greater than 25% of the foot's total length, said lateral and medial arcs being dimensioned such that at no point do they exceed the medial and lateral boundaries created by the foot itself, and said dome shaped structure having its entirety within the periphery set by the metatarsal heads, calcaneus, and lateral and medial borders of the foot.

3. A foot/arch rehabilitative insole or midsole unit as defined in claim 1 wherein the apex height of said dome shaped structure is between 5.28% and 7.6% of the total foot length.

4. A foot/arch rehabilitative insole or midsole unit as defined in claim 1 wherein said dome shaped structure displays density, compression and rebound characteristics such that when the dome shaped structure is subject to vertical forces of approximately 2.5 times body weight, said structure will deflect between 40% and 60% of its maximum height, and vertical forces equal to 1 body weight create no compression of said structure.

5. A foot/arch rehabilitative insole or midsole unit as defined in claim 1 comprising a body wherein the posterior aspect of said body is characterized by a tapered step, wherein the maximum step thickness corresponds with the sagittal plane midline of the calcaneus and tapers, in a posterior direction to a level equal to the minimum thickness of said body at the posterior most part of said body.

6. A foot/arch rehabilitative insole or midsole unit as defined in claim 5 wherein said body and said dome shaped structure are formed as a one piece unit.

7. A foot/arch rehabilitative insole or midsole unit as defined in claim 5 wherein said body and said dome shaped structure are formed as separate units and adhered together.

8. A foot/arch rehabilitative insole or midsole unit as defined in claim 2 wherein the apex height of said dome shaped structure is between 5.28% and 7.6% of the total foot length.

9. A foot/arch rehabilitative insole or midsole unit as defined in claim 2 wherein said dome shaped structure displays density, compression and rebound characteristics such that when the dome shaped structure is subject to vertical forces of approximately 2.5 times body weight, said structure will deflect between 40% and 60% of its maximum height, and vertical forces equal to 1 body weight create no compression of said structure.

10. A foot/arch rehabilitative insole or midsole unit as defined in claim 2 comprising a body wherein the posterior aspect of said body is characterized by a tapered step, wherein the maximum step thickness corresponds with the sagittal plane midline of the calcaneus and tapers, in a posterior direction, to a level equal to the minimum thickness of said body at the posterior most part of said body.

11. A foot/arch rehabilitative insole or midsole unit as defined in claim 10 wherein said body and said dome shaped structure are formed as a one piece unit.

12. A foot/arch rehabilitative insole or midsole unit as defined in claim 10 wherein said body and said dome shaped structure are formed as separate units and adhered together.

13. The insole or midsole unit of claim 1 which further comprises a body portion comprising a posterior most skiving for reducing impact velocity of the foot as it impacts on the ground, thereby causing the pressure exerted on the foot's arch system by said domed structure to be more gradual with consequent reduction of risk of impact related injury.

14. A method for promoting rehabilitation of the foot of an individual in need thereof, said method comprising fitting to the plantar aspect of the foot of said individual a rehabilitative mechanism comprising a domed shaped structure with an apex at a location approximating the anatomical apex of the individual's foot's arch system and corresponding with the articulation of the lateral cuneiform, cuboid, and navicular bones of the foot, and allowing said individual to utilize said rehabilitative mechanism by ambulation, including walking and/or running on the same, whereby upwardly directed pressure is created on the plantar aspect of the foot, at the arch region, while allowing uninhibited tri-planar movement of the foot about the apex of the dome functioning as a pivot point.

15. The method of claim 14 which further comprises determining the optimum density, compression and rebound characteristics of said domed structure for said individual, such that when said domed shaped structure is subjected to vertical forces common to ambulatory running of approximately 2.5 times body weight, the domed shaped structure will deflect between 40% and 60% of its maximum height, and when the domed shaped structure is subject to vertical forces of approximately 1 body weight there will be no compression of the domed shaped structure, and wherein the domed shaped structure is provided with an apex height which is between from 5.28% to 7.6% of the total foot length of said individual.

16. The method of claim 15 which further comprises monitoring the musculoskeletal remodeling of the foot of said individual during the course of treatment and replacing the proprioceptive rehabilitative catalyst one or more times as necessary in response to progressive musculoskeletal changes to maintain optimum compression, density and rebound characteristics of said domed shaped structure.

* * * * *